US009295435B2

(12) United States Patent
Florent et al.

(10) Patent No.: US 9,295,435 B2
(45) Date of Patent: Mar. 29, 2016

(54) IMAGE REPRESENTATION SUPPORTING THE ACCURATE POSITIONING OF AN INTERVENTION DEVICE IN VESSEL INTERVENTION PROCEDURES

(75) Inventors: Raoul Florent, Ville d'Avray (FR); Pascal Yves Francois Cathier, Asnieres-sur-Seine (FR); Olivier Pierre Nempont, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 199 days.

(21) Appl. No.: 13/983,155

(22) PCT Filed: Jan. 31, 2012

(86) PCT No.: PCT/IB2012/050441
§ 371 (c)(1),
(2), (4) Date: Aug. 1, 2013

(87) PCT Pub. No.: WO2012/107857
PCT Pub. Date: Aug. 16, 2012

(65) Prior Publication Data
US 2013/0308844 A1    Nov. 21, 2013

(30) Foreign Application Priority Data
Feb. 7, 2011    (EP) ..................................... 11305116

(51) Int. Cl.
*A61B 6/00*        (2006.01)
*A61B 6/12*        (2006.01)
(Continued)

(52) U.S. Cl.
CPC ................. *A61B 6/12* (2013.01); *A61B 5/0033* (2013.01); *A61B 6/481* (2013.01); *A61B 6/487* (2013.01);
(Continued)

(58) Field of Classification Search
CPC .. A61B 6/12; A61B 2019/5289; A61B 6/481; A61B 6/487; A61B 6/488; A61B 6/504; A61B 6/5229; A61B 2017/00778; A61B 2019/5238; A61B 5/0033; A61B 6/4441; G06T 7/0024; G06T 2207/10121; G06T 2207/20221; G06T 2207/30021; G06T 2207/30101
See application file for complete search history.

(56) References Cited

U.S. PATENT DOCUMENTS 5,570,430 A * 10/1996 Sheehan ............... G06T 7/0012
378/98.5
6,224,257 B1 * 5/2001 Launay et al. ................. 378/207
(Continued)

FOREIGN PATENT DOCUMENTS

WO    WO2010067300          6/2010
WO    WO 2010067300 A1 *  6/2010 ............... A61B 6/12

OTHER PUBLICATIONS

Cribier, "Percutaneous Implantation of Aortic Valve Prostheses in Patients With Calcific Aortic Stenosis—Technical Advances", Valve Replacement & Repair, Interventional Cardiology, Oct. 2007, pp. 68-69.

*Primary Examiner* — Manav Seth (57) ABSTRACT

A medical imaging device and a method for providing an image representation supporting inaccurate positioning of an intervention device in a vessel intervention procedure is proposed. Therein, an anatomy representation (AR) of a vessel region of interest and at least one angiogram X-ray image (RA) and a live fluoroscopy X-ray image (LI) are acquired. The following steps are performed when a radio-opaque device is fixedly arranged within the vessel region of interest: (a) registering the anatomy representation to the at least one angiogram X-ray image in order to provide an anatomy-angiogram-registration (R1); (b) processing (DP) the at least one angiogram X-ray image and the at least one live fluoroscopy X-ray image in order to identify in each of the X-ray images the radio-opaque device; (c) registering (R2) the at least one angiogram X-ray image to the at least one live fluoroscopy X-ray image based on the identified radio-opaque device in order to provide an angiogram-fluoroscopy-registration; and (d) combining the anatomy-angiogram-registration and the angiogram-fluoroscopy-registration in order to provide an anatomy-fluoroscopy-registration (GTC; RALC). Finally, an image representation resulting from the anatomy-fluoroscopy-registration showing an overlay of live images with the anatomy representation may be output thereby helping a surgeon to accurately position for example a synthetic aortic valve within an aortic root of a heart.

20 Claims, 3 Drawing Sheets

(51) Int. Cl.
*G06T 7/00* (2006.01)
*A61B 5/00* (2006.01)
*A61B 17/00* (2006.01)
*A61B 19/00* (2006.01)

(52) U.S. Cl.
CPC .............. *A61B 6/504* (2013.01); *A61B 6/5229* (2013.01); *G06T 7/0024* (2013.01); *A61B 6/4441* (2013.01); *A61B 6/488* (2013.01); *A61B 2017/00778* (2013.01); *A61B 2019/5238* (2013.01); *A61B 2019/5289* (2013.01); *G06T 2207/10121* (2013.01); *G06T 2207/20221* (2013.01); *G06T 2207/30021* (2013.01); *G06T 2207/30101* (2013.01)

(56) References Cited

U.S. PATENT DOCUMENTS

| | | | | |
|---|---|---|---|---|
| 6,493,575 | B1 * | 12/2002 | Kesten | A61B 19/52 600/431 |
| 7,010,080 | B2 | 3/2006 | Mitschke et al. | |
| 7,190,819 | B2 * | 3/2007 | Viswanathan | G06K 9/00 382/128 |
| 7,267,650 | B2 * | 9/2007 | Chow | A61B 8/12 600/467 |
| 7,409,078 | B2 * | 8/2008 | Pescatore | G06T 3/0068 382/130 |
| 7,853,061 | B2 * | 12/2010 | Gorges | G06T 15/503 378/190 |
| 7,907,989 | B2 * | 3/2011 | Borgert | A61B 5/06 382/128 |
| 8,000,507 | B2 * | 8/2011 | Rongen | A61B 6/469 382/128 |
| 8,060,186 | B2 * | 11/2011 | Mohamed | A61B 19/50 600/424 |
| 8,126,241 | B2 * | 2/2012 | Zarkh | A61B 6/12 382/131 |
| 8,208,701 | B2 * | 6/2012 | Lendl | A61B 6/12 382/128 |
| 8,295,577 | B2 * | 10/2012 | Zarkh | A61B 6/12 382/132 |
| 8,311,308 | B2 * | 11/2012 | Chen | G06K 9/4614 378/42 |
| 8,989,461 | B2 * | 3/2015 | Zhu | G06K 9/6207 382/128 |
| 2002/0172323 | A1 * | 11/2002 | Karellas | G01F 1/66 378/51 |
| 2004/0116809 | A1 * | 6/2004 | Chow | A61B 8/12 600/439 |
| 2006/0036167 | A1 * | 2/2006 | Shina | A61B 6/12 600/433 |
| 2006/0262970 | A1 | 11/2006 | Boese et al. | |
| 2007/0167721 | A1 | 7/2007 | Pfister et al. | |
| 2007/0197905 | A1 * | 8/2007 | Timinger | A61B 5/06 600/424 |
| 2008/0167714 | A1 | 7/2008 | St. Goar et al. | |
| 2008/0247621 | A1 * | 10/2008 | Zarkh | A61B 6/12 382/130 |
| 2009/0087068 | A1 | 4/2009 | Sakaguchi | |
| 2009/0088830 | A1 * | 4/2009 | Mohamed | A61B 19/50 623/1.11 |
| 2010/0161022 | A1 | 6/2010 | Tolkowsky | |
| 2010/0228076 | A1 | 9/2010 | Blank et al. | |
| 2010/0249918 | A1 | 9/2010 | Zhang | |
| 2010/0312100 | A1 * | 12/2010 | Zarkh | A61B 6/12 600/424 |
| 2012/0177277 | A1 | 7/2012 | Florent et al. | |

\* cited by examiner

IMAGE REPRESENTATION SUPPORTING THE ACCURATE POSITIONING OF AN INTERVENTION DEVICE IN VESSEL INTERVENTION PROCEDURES

CROSS-REFERENCE TO PRIOR APPLICATIONS

This application is the U.S. National Phase application under 35 U.S.C. §371 of International Application Serial No. PCT/IB2012/050441, filed on Jan. 31, 2012, which claims the benefit of European Application Serial No. 11305116.3, filed on Feb. 7, 2011. These applications are hereby incorporated by reference herein.

FIELD OF THE INVENTION

The present invention relates to a medical imaging device and a method for providing an image representation supporting the accurate positioning of an intervention device such as an artificialaortic valve in a vessel intervention procedure such as transcatheter aortic valve implantation (TAVI). Furthermore, the present invention relates to a corresponding catheterization laboratory system, a corresponding computer program and a computer-readable medium comprising such computer program.

BACKGROUND OF THE INVENTION

Vessel intervention procedures often comprise the task of positioning an intervention device inside a vessel prior to further procedural steps. For example, in TAVI interventions, a very critical point is the precise positioning of an implantable device under fluoroscopy prior to fixation or deployment of the implantable device. To achieve such positioning, an angiogram, i.e. an X-ray image acquisition with contrast agent being present in a vessel region of interest, is typically performed in order to determine an optimal projection for fixation of the implantable device, i.e. for example for deployment of a replacement aortic valve. An image featuring for example good contrast may be manually selected, stored and subsequently used as pre-implant reference image. The contrast agent injection may be achieved through a so-called pig-tail catheter placed in the aortic root.

In order to facilitate accurate positioning, road mapping or outlining methods have been proposed e.g. in WO 2010067300 A1. Therein, a live view, i.e. a fluoroscopy X-ray image without contrast agent being present in the vessel region of interest, may be superimposed with an anatomic representation of the aortic root such as contours of the aortic root as extracted from a reference aortogram, a model derived from 3D-pre-interventional data, combinations thereof, etc. The anatomic representation should be correctly registered to the live images, such live registration process being often referred to as tracking.

SUMMARY OF THE INVENTION

Because features of the vessel anatomy such as e.g. a valve anatomy may be hardly visible in live fluoroscopy X-ray images, a registration of the anatomic representation with the life data may be very challenging.

There may be a need for a medical imaging device implementing a robust method for a registration process of an anatomic representation to live data.

Such need may be met with the subject-matter of the independent claims. Further embodiments of the invention are defined in the dependent claims.

According to an aspect of the present invention, a medical imaging device for providing an image representation supporting the accurate positioning of an intervention device in a vessel intervention procedure is proposed. The medical imaging device is adapted to perform the following steps, preferably but not exclusively in the indicated order:

(i) acquiring an anatomy representation of a vessel region of interest from an anatomy representation providing device;

(ii) acquiring at least one angiogram X-ray image of the vessel region of interest with contrast agent injected into the vessel and acquiring at least one live fluoroscopy X-ray image of the vessel region of interest without contrast agent injected into the vessel wherein both, the angiogram X-ray image and the live fluoroscopy X-ray image, may be acquired from at least one X-ray image acquiring device;

(iii) performing the following process steps:
  (a) registering the anatomy representation to the at least one angiogram X-ray image in order to provide an anatomy-angiogram-registration;
  (b) processing the at least one angiogram X-ray image and the at least one live fluoroscopy X-ray image in order to identify in each of the angiogram X-ray image and the live fluoroscopy X-ray image a radio-opaque device being arranged such as to be spatially correlated with the vessel region of interest, e.g. being fixedly arranged within the vessel region of interest;
  (c) registering the at least one angiogram X-ray image to the at least one live fluoroscopy X-ray image based on the identified radio-opaque device in order to provide an angiogram-fluoroscopy-registration; and
  (d) combining the anatomy-angiogram-registration and the angiogram-fluoroscopy-registration in order to provide an anatomy-fluoroscopy-registration;

(iv) outputting an image representation resulting from the anatomy-fluoroscopy-registration.

A gist of the present invention may be explained with reference to transcatheter aortic valve implantation as a specific example of a vessel intervention procedure in which a replacement aortic valve shall be accurately positioned within an aortic root. In such TAVI the accurate registration of an anatomy representation derived from pre- or peri-interventional data with live fluoroscopy images may be instrumental for fine valve positioning. However, since the anatomy may be hardly visible in the fluoroscopy life images, such life registration process (tracking) may be challenging. It is therefore proposed to enforce a locking of a radio-opaque device such as a pig-tail catheter into one sinus of the aortic root such that this radio-opaque device is moving in coherence with the aorta and the valve anatomy. The radio-opaque device may then be processed and identified in both, a reference aortogram (i.e. an angiogram X-ray image of the aortic vessel region of interest) and the live fluoroscopy images of the vessel region of interest in order to act as a mediator in the spatial registration of the anatomy representation and the live views.

In the following, possible features and advantages of embodiments of the invention will be presented.

The anatomy representation as acquired by the proposed medical imaging device may be or may be derived from a two-dimensional or three-dimensional data set acquired pre-interventional, i.e. prior to the vessel intervention procedure. For example, the anatomy representation may be derived from a computer tomography (CT) scan.

Especially in TAVI interventional procedures, the vessel region of interest may be a region surrounding an aortic root of a heart in which a replacement aortic valve shall be achieved. In such case, the radio-opaque device may be arranged and locked in one of the valve sinus, this being a typical anatomic spot where e.g. a catheter may safely be locked at least up to a valve deployment time. Thus, the radio-opaque device may be fixedly connected to the aortic valve such that the device and the valve anatomy are tightly spatially connected such as to move in conjunction during a cardiac cycle.

The radio-opaque device may be a pig-tail catheter as is routinely used for contrast agent injection when producing for example angiograms.

The at least one angiogram X-ray image and the at least one live fluoroscopy X-ray image may be acquired with a same X-ray image acquiring device being in an identical image acquisition geometry. In other words, in a vessel intervention procedure, first the angiogram X-ray image may be acquired using an X-ray image acquisition device while contrast agent is present within the vessel region of interest. At a later stage of the procedure, i.e. when the intervention device such as a replacement aortic valve is to be positioned within the vessel region of interest, one or more live fluoroscopy X-ray images may be acquired without any contrast agent present within the vessel region of interest using the same X-ray image acquiring device, wherein the image acquisition geometry is the same as when taking the angiogram X-ray image. Furthermore, the radio-opaque device should be at the same position within the vessel region of interest for both the angiogram X-ray image acquisition and the live fluoroscopy X-ray image acquisition. Thus, upon the radio-opaque device being identified in each of the angiogram X-ray image and the live fluoroscopy X-ray image, the two X-ray images may be easily registered to one another in order to generate the angiogram-fluoroscopy-registration.

In order to optimize a subsequent provision of the angiogram-fluoroscopy-registration, the proposed medical imaging device may be adapted to acquire not only a single but a plurality of angiogram X-ray images. Then, at least one specific one of the plurality of angiogram X-ray images may be selected for the subsequent angiogram-fluoroscopy-registration. For example, only one specific image from an angiogram image sequence may be selected, this image representing e.g. a best contrast-agent filled state, a particular cardiac phase or any other advantageous criteria for optimizing the subsequent provision of the angiogram-fluoroscopy-registration. Alternatively, a plurality of angiogram X-ray images constituting a portion of a cardiac cycle or a full cardiac cycle may be selected from the angiogram image sequence.

Alternatively several angiogram image sequences may be acquired with various geometries. Those several angiogram sequences might be conjointly used to register the anatomy representation within a given frame of reference, for instance the frame of reference of the operating room, and one of those angiogram sequence should contain the radio-opaque device and be used in the registration with the live image from the device identification.

In order to identify the radio-opaque device within the vessel region of interest in each angiogram X-ray image and the live fluoroscopy X-ray image, a segmentation technique or a feature analysis technique may be used. In other words, using such technique the position, orientation and/or outline of the radio-opaque device may be found in the X-ray images and may subsequently be used for registering the images. The identification process may also use a "fuzzy identification" that amounts to computing pixel-based measurements indicating, for each pixel, how likely it is that this pixel belongs to the targeted device.

In order to further support the accurate positioning of the intervention device in the vessel intervention procedure, the proposed medical imaging device may be further adapted for generating visualized positioning marks within the output image representation. For example, an outline of the valve as projected onto the image plane may be visualized within the image representation resulting from the anatomy-fluoroscopy-registration. In addition to the pure anatomy information, this image representation may further include geometrical elements such as a schematic representation of the valve plane (seen in projection as a line or a parallelogram, or a simple shape such as a circle or an ellipse), which may be a key element for valve fine positioning.

The proposed medical imaging device may be applied in X-ray catheterization laboratory systems as used potentially in an operation room environment. Furthermore, it may also be exploited in other situations where device-mediated registration may be meaningful.

According to a further aspect of the present invention, a computer program or a computer program element is proposed that is characterized by being adapted to execute the method steps as defined above with respect to the proposed medical imaging device when executed on an appropriate computing device or programmable system. In fact, a computing device or programmable system on which such computer program is executed and which furthermore comprises for example suitable interfaces, processors and memory for acquiring the respective anatomy representation data and X-ray image data as an input for subsequent data processing for providing the anatomy-angiogram-registration, the angiogram-fluoroscopy-registration and finally the anatomy-fluoroscopy-registration, may be operative as the above-defined medical imaging device.

According to a further aspect of the present invention, a computer-readable medium such as a CD-ROM is presented wherein the computer-readable medium has a computer program as described in the preceding section stored thereon. However, the computer program may also be presented over a network and may be downloaded into the working memory of a data processor from such network. Accordingly, the computer-readable medium may be a medium for making a computer program available for downloading.

It has to be noted that features and advantages of embodiments of the invention are described herein with reference to different subject-matters. In particular, some embodiments are described with respect to method type features whereas other embodiments are described with respect to device type features. However, a person skilled in the art will gather from the above and the following description that, unless otherwise notified, in addition to any combination of features belonging to one type of subject-matter also any combination between features relating to different subject-matters is considered to be disclosed with this application. Particularly, features can be combined providing synergic effects that are more than the simple sum of the features.

BRIEF DESCRIPTION OF THE DRAWINGS

The features and embodiments defined above and further features and advantages of the present invention can also be derived from the examples of embodiments to be described herein after and are explained with reference to examples of embodiments, but to which the invention is not limited. The invention will be described in more detail hereinafter with reference to the drawings.

The figures are only schematically and not to scale.

DETAILED DESCRIPTION OF EMBODIMENTS

Figure 1:
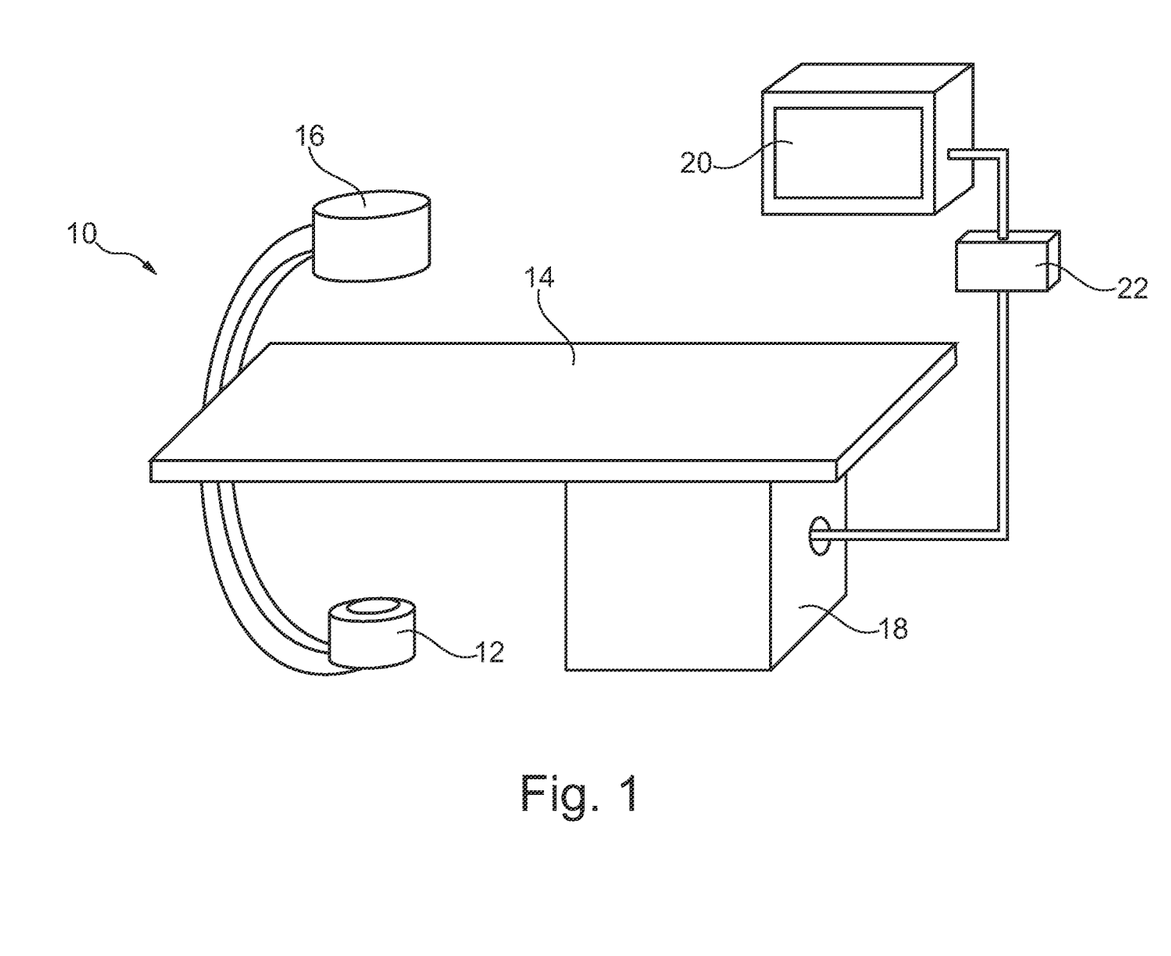
FIG. 1 shows an X-ray imaging system for the use in a catheterization laboratory for accurate positioning for vessel intervention procedures.

FIG. 1 schematically shows an X-ray imaging system 10 for use in a catheterization laboratory with an examination apparatus for accurate positioning for heart valve replacement. The examination apparatus comprises an X-ray image acquisition device with a X-ray source 12 provided to generate X-ray radiation. A table 14 is provided to receive a patient to be examined. Further, an X-ray image detection module 16 is located opposite the X-ray source 12, i.e. during the radiation procedure the subject is located between the X-ray source 12 and the detection module 16. The latter is sending data to a data processing unit 18, which is connected to both the detection module 16 and the X-ray source 12. Furthermore a display device 20 is arranged in the vicinity of the table 14 to display information to the person operating the X-ray imaging system, i.e. a clinician such as a cardiologist or cardiac surgeon. Preferably the display device 20 is movably mounted to allow for an individual adjustment depending on the examination situation. Also, an interface unit 22 is arranged to input information by the user. Basically, the X-ray source 12 and the image detection module 16 generate images by exposing the patient to X-ray radiation, wherein said images are further processed in the data processing unit 18. It is noted that the example shown is of a so-called C-type X-ray image acquisition device. Of course, the invention also relates to other types of X-ray image acquisition devices.

The procedure according to the invention is described in more detail below and may be implemented e.g. in the data processing device 18 which may then form a medical imaging device according to an embodiment of the present invention.

According to the invention, the image acquisition device shown in FIG. 1 is adapted to acquire at least one angiogram X-ray image of a vessel region of interest with injected contrast agent and to acquire at least one live fluoroscopy image of the vessel region of interest. Both X-ray images may be transmitted to the data processing unit 18. The data processing unit 18 is adapted to identify information data within both acquired images to identify or detect a radio-opaque device which has been previously introduced into the vessel region of interest.

The data processing unit 18 is also adapted to register the vessel representation of the angiogram X-ray image with the fluoroscopy X-ray image, wherein the information on the identified radio-opaque device is used for such registration process.

Furthermore, the processing device may be adapted to acquire or import and store an anatomy representation of the vessel region of interest which has been acquired prior to the vessel intervention procedure using e.g. a CT scan and to register this anatomy representation with the at least one angiogram X-ray image.

From these two registration steps, a final registration of the anatomy representation with the live fluoroscopy image may be generated and displayed on the display 20 in order to support the surgeon in accurately positioning the replacement aortic valve.

Since treatment of heart valve problems or heart valve diseases becomes more important, because of an ageing population, wherein such diseases usually require the replacement of a native heart valve, the invention provides a cardiologist or surgeon with better information, for example, during percutaneous heart valve implantation. Although the invention is exemplarily described in relation with the replacement of the aortic valve, the invention may also relate to the replacement of other types of heart valves, such as pulmonary, mitral and tricuspid valves. Of course, the invention may also relate to other vessel treatments, for example inserting a stent, for example, in vessel region with a defected vessel cross section. Another example is the Abdominal Aortic Aneurysm (AAA) endo-treatment called EVAR (Endo-Vascular Aortic Aneurysm Repair), where the pigtail can be locked into the renal artery.

Figure 2:
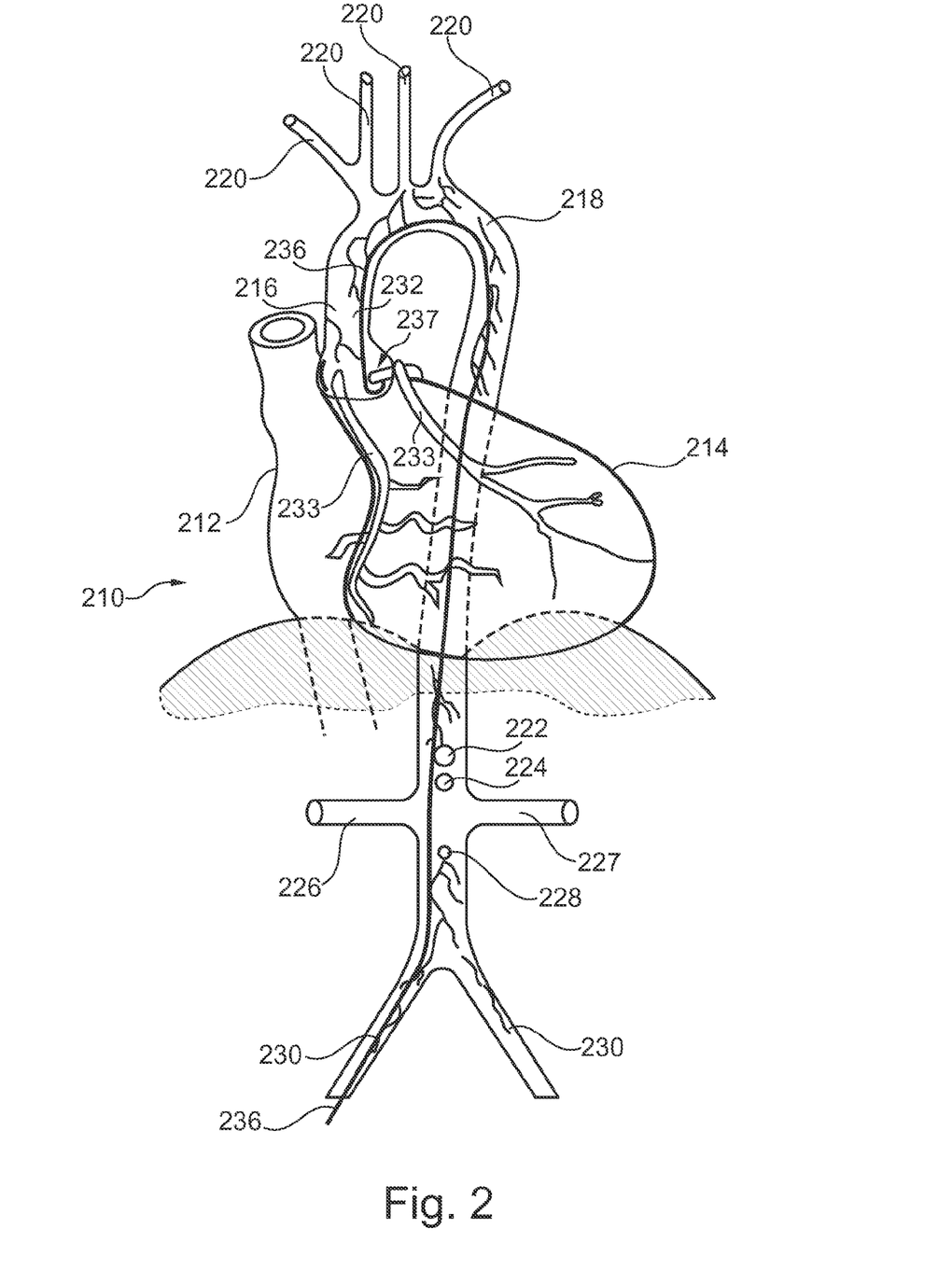
FIG. 2 shows the structure of the aorta with an intervention device arranged therein.

In FIG. 2, a heart 210 is shown with a right part 212 and a left part 214 in relation to the main vessels. The right part 212 is placed on the vena cava in the diagram. It should designate the part of the heart irrigated by the right coronary. On top of the left part, an ascending aorta 216 can be seen forming an arch 218 where several other vessels 220 are connected to the aorta 216. The aorta 216 then leads downwards where several further vessels are connected, such as the celiac artery 222 and the superior mesenteric artery 224. Still further, the aorta splits up into the renal arteries 226 and the inferior mesenteric artery 228 and the iliac arteries 230. This part is also called the abdominal aorta. The connection point to the heart itself, so to speak the starting point of the aorta 216 is the root 232 or aortic root. Further, two coronary arteries 233 are connected in the root region 230. An aortic heart valve which is not shown in FIG. 2 is located at the root 232.

For a heart valve replacement such as the replacement of the aorta valve located at the root 232, a valve delivery catheter may be inserted in the groin into one of the iliac arteries 230 and threaded up to the heart valve to be replaced. In other words, the catheter follows the aorta passing the arch 218 until it reaches the root region 232 where the valve may be deployed after correct positioning.

By providing the surgeon with displaying a composite image representation generated according to the method steps described herein, the surgeon is provided with improved or enhanced information about the localization or positioning respectively of the catheter or another positioning tool for bringing the artificial heart valve into the correct position.

Thus, the displayed composite image representation provide the cardiac surgeon or cardiologist with the information needed for a correct deployment an artificial valve.

For actual, respectively current, information it is possible to repeat the fluoroscopy image acquisition in a predetermined interval. Usually, the fluoroscopy acquisition step is undertaken without the use of contrast agent. By providing the surgeon with the composite image according to the invention, it is possible, to reduce the amount of contrast agent used during the interventional procedure which may mean a great relief for patients who have kidney problems, for example.

Figure 3:
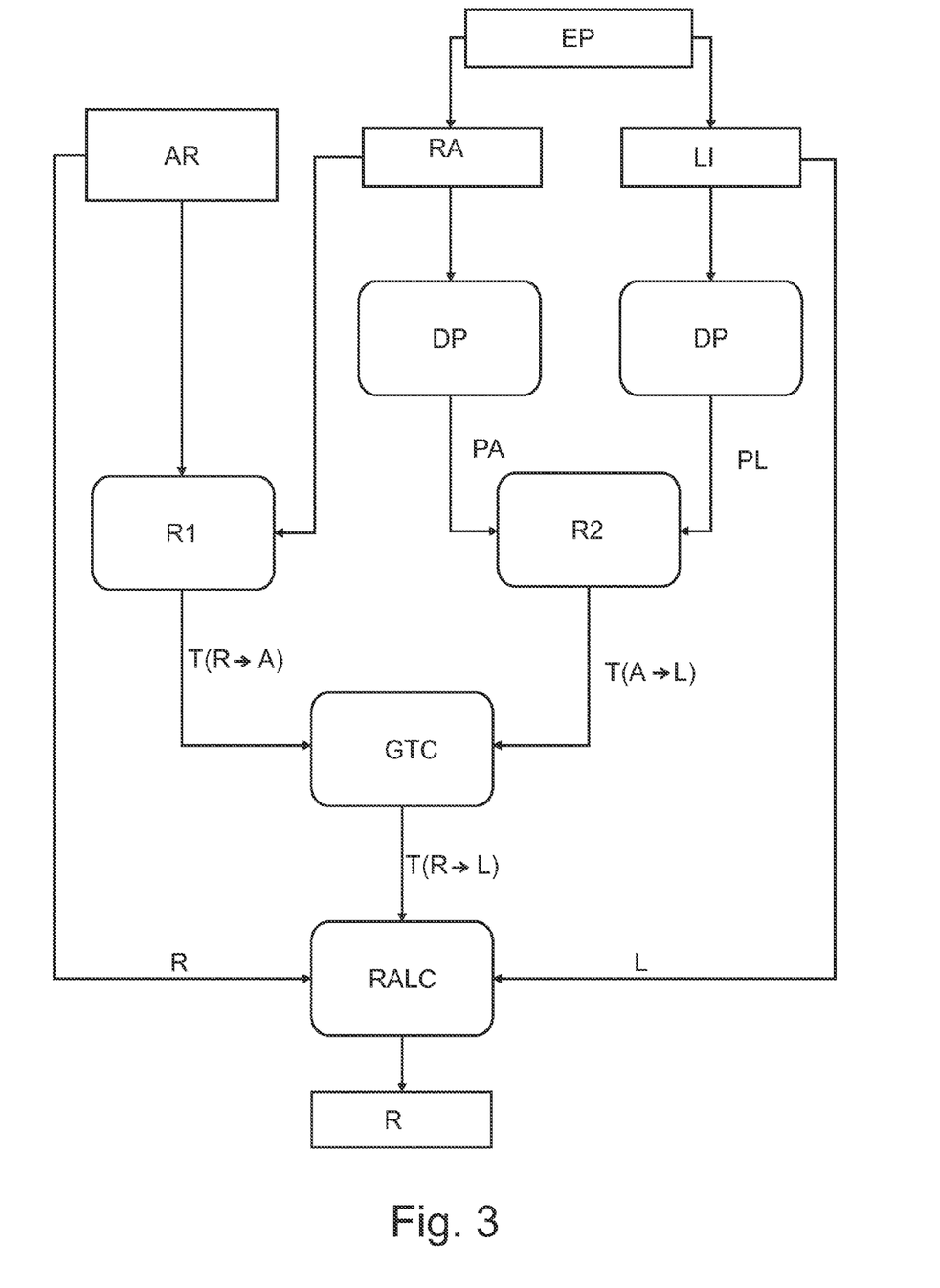
FIG. 3 shows a chart describing the method steps performed by a medical imaging device according to the invention.

In the following, the main processing steps performed in a medical imaging device according to an embodiment of the inventions are described with respect to FIG. 3:

The medical imaging device requires the following data inputs:

(i) An Anatomy Representation (AR): This typically describes the valve and its surrounding. It can be derived from a pre-interventional 3D data set, for instance from a CT scan. In this case the representation can include a 3D representation of the aortic root, of the various valve elements, of the possible calcification spots surrounding the valve, etc. . . . . The representation can also combine elements derived from pre- and peri-interventional sources.

(ii) An Enforcement protocol (EP): This entry symbolically represents one aspect of the invention that consists in enforcing both at angiogram and live fluoroscopy X-ray image acquisition times the locking of the radio-opaque device (typically a pig-tail catheter or any intervention-relevant radio-opaque device) in a location that is spatially tightly connected to the target anatomy (the valve and aortic root). A valve sinus (FIG. 2) is typically an anatomic location where such a locking may be readily achieved. In practice this spot is already used for the "parking" of the pig-tail catheter. The radio-opaque device can stay in place, up to the valve final deployment, where it should be removed if one does not want to face device jailing. But this means that the device can stay put during the full fine placement phase.

(iii) A Reference Aortogram (RA): This is a typical aortogram as routinely achieved in this kind of intervention in order to assess the situation. There might be a constraint that it fulfils the enforcement protocol, and that it corresponds to the same acquisition geometry as the subsequent fluoroscopy. In fact only a fraction of the originating aortogram is considered here. This can be only one selected image of the aortogram (best contrast-agent filled, in a particular cardiac phase, other criteria, etc.), or it can be constituted by a full cardiac cycle extracted from the full aortogram (best injected cardiac cycle).

(iv) Live images (LI): They are constituted by consecutive fluoroscopy sequences which are in particular used to achieve fine device placement and the final deployment. As indicated in the figure, this entry is also subjected to the enforcement protocol.

Using these data inputs the medical imaging device may perform the following processing steps:

(a) Anatomy Representation to aortogram registration (R1): The anatomy-representation is brought into spatial coherence with the reference aortogram. If the anatomy-representation is derived from 3D peri-interventional data, then the registration might be complex and might be incomplete (for instance 3D-2D registration with depth incertitude), but sufficient to insure the correct matching of the two data sets. Traditional methods such as Hough-transform based, parametric least-square methods, etc. can be involved in this process. The result is a geometrical transform $T(R \rightarrow A)$. If the aortogram is a selection of several images such as for instance constituting a full cardiac cycle, this registration step might be applied to all the images of the aortogram, producing a set of geometrical transforms (one per aortogram image). Depending on the actual registration method involved, the geometrical transform $T(R \rightarrow A)$ might be expressed in a variety of ways, for instance as a parametric transform whose parameters are computed in the registration process, or as a full vector field defined for every pixel or voxel of R and pointing to a location of A that might lie between actual pixels of A, thus requiring data interpolation a transform time. The inverse transform $T(A \rightarrow R)$ linking the aortogram to the anatomy representation might also be made available in this process. Alternatively several angiogram image sequences may be acquired with various geometries. Those several angiogram sequences might be conjointly used to register the anatomy representation within a given frame of reference (for instance the frame of reference of the operating room), and one of those angiogram sequence must contain the radio-opaque device and is defined as the reference angiogram. Using several angiogram sequencing corresponding to different acquisition geometries usually produces better registration accuracy. Once the anatomy representation is registered in the given frame of reference, the transformation $T(R \rightarrow A)$ can be obtained using the acquisition geometry of the reference angiogram within the given frame of reference.

(b) Device processing (DP) in both the input aortogram (RA) and live fluoroscopy images (LI): The locked radio-opaque device is processed in both the input aortogram and live fluoroscopy images in order to produce the necessary material for subsequent registration. At this stage one typically resorts either to hard segmentation using e.g. device's footprint identification or to feature extraction using e.g. ridgeness, direction, etc. In the later case, the result might be constituted by a pixel-level measurement map, where, at each pixel, the measurement indicates the likelihood or probability for this pixel to belong to the targeted device. The resulting material may be respectively called Processed Aortogram (PA) and Processed Live images (PL). If the aortogram is constituted of several images, PA might contain the output of the processing of all the aortogram images. For the live entry, every fluoroscopy image is to be processed. The two processing steps DP, though both aiming at the binary or fuzzy identification of the radio-opaque device, might however be different whether they apply to angiogram data or to the live fluoroscopy data.

(c) Aortogram to live fluoroscopy image registration (R2): Based on material PA and PL, the images of aortogram and live entry may be brought into spatial correspondence. Typical registration methods can be involved at this step that exploits the device-originated data. If PA corresponds to a full cardiac cycle, cardiac phase pairing might be included in this process. But a global sequence to sequence registration step might also be considered. In any case, for every live fluoroscopy image, a registration geometrical transform is produced $T(A \rightarrow L)$ that links this image to one of the aortogram images (if several of them). Depending of the actual registration method involved, the geometrical transform $T(A \rightarrow L)$ might be expressed in a variety of ways, for instance as a parametric transform whose parameters are computed in the registration process, or as a full vector field defined for every pixel of A and pointing to a location of L that might lie between actual pixels of L, thus requiring data interpolation at transform time. The inverse transform $T(L \rightarrow A)$ linking the live data to the aortogram might also be made available in this process.

(d) Geometrical transform combination (GTC): The transforms $T(R \rightarrow A)$ and $T(A \rightarrow L)$ can then be algebraically combined so as to derive the transforms $T(R \rightarrow L)$ linking the representation-anatomy to the live images: $T(R \rightarrow L) = T(R \rightarrow A) \otimes T(A \rightarrow L)$. In this process, the actual direct transforms $T(R \rightarrow A)$ and $T(A \rightarrow L)$ and/or there reverse counterparts $T(A \rightarrow R)$ and $T(L \rightarrow A)$ might be involved. The resulting geometrical transform $T(R \rightarrow L)$ might be expressed in a variety of ways, for instance as a parametric transform or as a full warping field. The inverse transform $T(L \rightarrow R)$ might be made available in this process.

(e) Registered Anatomy Representation & Live image combination (RALC): After the application of $T(R \rightarrow L)$, the anatomy-representation is brought into spatial correspondence with the live images. The subsequent combination/merging of both the data streams can then occur.

The result (R) is typically the live fluoroscopy image sequences on which the registered anatomy-representation is overlaid in one way or another. For instance the outline of the valve as projected onto the image plane can be visualized.

Finally, it is to be noted that herein the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does

LIST OF REFERENCE SIGNS

10 X-ray imaging system
12 X-ray Source
14 Table
16 X-ray detection module
18 Data processing unit
20 Display device
22 Interface unit
210 Heart
212 Right part of the heart
214 Left part of the heart
216 Aorta
218 Art
220 Other vessels
222 Celiac artery
224 Superior mesenteric artery
226 Renal arteries
228 Inferior mesenteric artery
230 Iliac artery
232 Aortic root
233 Coronary arteries
236 Pig-tail catheter
237 aortic sinus

The invention claimed is:

1. A medical imaging device for providing an image representation supporting accurate positioning of an intervention device in a vessel intervention procedure, the medical imaging device comprising one or more processors being adapted for:
(i) from an anatomy representation providing device, acquiring an anatomy representation of a region of interest of a blood vessel;
(ii) from at least one X-ray image acquiring device, acquiring at least one angiogram X-ray image of the vessel region of interest with contrast agent injected into the vessel and acquiring at least one live fluoroscopy X-ray image of the vessel region of interest without contrast agent injected into the vessel;
(iii) performing the following process steps:
registering the anatomy representation to the at least one angiogram X-ray image in order to provide an anatomy-angiogram-registration;
processing the at least one angiogram X-ray image and the at least one live fluoroscopy X-ray image in order to identify in each of the angiogram X-ray image and the live fluoroscopy X-ray image a radio-opaque device;
registering the at least one angiogram X-ray image to the at least one live fluoroscopy X-ray image based on the identified radio-opaque device in order to provide an angiogram-fluoroscopy-registration; and
combining the anatomy-angiogram-registration and the angiogram-fluoroscopy-registration in order to provide an anatomy-fluoroscopy-registration; and
(iv) outputting an image representation resulting from the anatomy-fluoroscopy-registration.

2. The medical imaging device of claim 1, said at least one X-ray image acquiring device constituting a set, said set being configured for said acquiring of said at least one angiogram X-ray image and of said at least one live fluoroscopy X-ray image.

3. The medical imaging device of claim 2, further comprising:
a first circuit for performing said registering to provide said anatomy-angiogram-registration, said processing, said registering to provide said angiogram-fluoroscopy-registration, and said combining; and
a second circuit configured for said outputting.

4. The medical imaging device of claim 3, wherein said registering the at least one angiogram X-ray image is performed based on the identifying of said radio-opaque device in said each image.

5. The medical imaging device of claim 4, wherein the acquired anatomy representation is derived from one of a 2-dimensional data set and a 3-dimensional data set acquired pre-interventional.

6. The medical imaging device of claim 4, wherein the acquired anatomy representation is derived from a computed tomography (CT) scan.

7. The medical imaging device of claim 4, wherein the radio-opaque device is a pig-tail catheter.

8. The medical imaging device of claim 4, wherein said medical imaging device is further adapted for acquiring several angiogram sequences under various acquisition geometries, wherein one of the sequences contains the radio-opaque device being arranged such as to be spatially correlated with the vessel region of interest and wherein the one of the sequences is chosen as a reference angiogram, and wherein the several angiogram sequences are used to compute the anatomy-angiogram-registration corresponding to the reference angiogram.

9. The medical imaging device of claim 4, wherein a plurality of angiogram X-ray images are acquired and at least one of the plurality of angiogram X-ray images is selected for optimized subsequent providing of the angiogram-fluoroscopy-registration.

10. The medical imaging device of claim 4, wherein the radio-opaque device is identified in the vessel region of interest using one of a segmentation and a feature analysis method.

11. The medical imaging device of claim 4, wherein the device is further adapted for generating visualized positioning marks within the output image representation for further supporting in accurate positioning of an intervention device in a vessel intervention procedure.

12. A catheterization laboratory system comprising the medical imaging device of claim 4.

13. The medical imaging device of claim 1, comprising:
a CT scanner as said anatomy representation providing device;
an X-ray scanner as said at least one X-ray image acquiring device;
circuitry for said performing; and
a display device for said outputting.

14. A medical imaging device for providing an image representation supporting accurate positioning of an intervention device in a vessel intervention procedure, the medical imaging device comprising one or more processors being adapted for:
(i) acquiring an anatomy representation (AR) of a vessel region of interest from an anatomy representation providing device;
(ii) acquiring at least one angiogram X-ray image (RA) of the vessel region of interest with contrast agent injected into the vessel and acquiring at least one live fluoroscopy X-ray image (LI) of the vessel region of interest without contrast agent injected into the vessel from at least one X-ray image acquiring device;

(iii) performing the following process steps:
  registering (R1) the anatomy representation (AR) to the at least one angiogram X-ray image (RA) in order to provide an anatomy-angiogram-registration;
  processing (DP) the at least one angiogram X-ray image and the at least one live fluoroscopy X-ray image in order to identify in each of the angiogram X-ray image (RA) and the live fluoroscopy X-ray image (LI) a radio-opaque device being arranged such as to be spatially correlated with the vessel region of interest;
  registering (R2) the at least one angiogram X-ray image (RA) to the at least one live fluoroscopy X-ray image (LI) based on the identified radio-opaque device in order to provide an angiogram-fluoroscopy-registration; and
  combining (GTC, RALC) the anatomy-angiogram-registrations and the angiogram-fluoroscopy-registration in order to provide an anatomy-fluoroscopy-registration; and
(iv) outputting an image representation resulting from the anatomy-fluoroscopy-registration,
wherein the angiogram X-ray image and the at least one live fluoroscopy X-ray image are acquired with a same X-ray image acquiring device being in an identical image acquisition geometry.

15. A method for providing an image representation supporting accurate positioning of an intervention device in a vessel intervention procedure, the method comprising:
  (i) from an anatomy representation providing device, acquiring an anatomy representation of a region of interest of a vessel;
  (ii) from at least one X-ray image acquiring device, acquiring at least one angiogram X-ray image of the vessel region of interest with contrast agent injected into the vessel and acquiring at least one live fluoroscopy X-ray image of the vessel region of interest without contrast agent injected into the vessel;
  (iii) performing the following process steps:
    registering the anatomy representation to the at least one angiogram X-ray image in order to provide an anatomy-angiogram-registration;
    processing, by a data processor, the at least one angiogram X-ray image and the at least one live fluoroscopy X-ray image in order to identify in each of the angiogram X-ray image and the live fluoroscopy X-ray image a radio-opaque device;
    registering the at least one angiogram X-ray image to the at least one live fluoroscopy X-ray image based on the radio-opaque device identified in said each image by said data processor in order to provide an angiogram-fluoroscopy-registration; and
    combining the anatomy-angiogram-registration and the angiogram-fluoroscopy-registration in order to provide an anatomy-fluoroscopy-registration; and
  iv) outputting an image representation resulting from the anatomy-fluoroscopy-registration.

16. The method of claim 15, among said plurality there being the further act of:
  arranging said radio-opaque device so as to be, at respective times of said acquiring of said each image, tightly spatially connected to said blood vessel.

17. The method of claim 16, wherein the tightness of the connection is such that, at the connection, said radio-opaque device moves in conjunction with said blood vessel during a cardiac cycle.

18. The medical imaging device of claim 16, wherein the tightness of the connection is such that, at the connection, said radio-opaque device moves coherently with said blood vessel during a cardiac cycle.

19. The method of claim 15, wherein the vessel region of interest is a region surrounding an aortic root.

20. A non-transitory computer readable medium embodying a computer program for providing an image representation supporting accurate positioning of an intervention device in a vessel intervention procedure, said computer program having instructions executable by a processor for performing a plurality of acts, from among said plurality there being the acts of:
  processing, by a data processor, at least one angiogram X-ray image of a region of interest of a vessel with contrast agent injected into the vessel and at least one live fluoroscopy X-ray image of the vessel region of interest without contrast agent injected in the vessel in order to identify in each of the angiogram X-ray image and the live fluoroscopy X-ray image a radio-opaque device;
  in order to provide an angiogram-fluoroscopy-registration, registering by said data processor the at least one angiogram X-ray image to the at least one live fluoroscopy X-ray image, the angiogram-fluoroscopy-registration in order to provide an anatomy-fluoroscopy-registration; and
  outputting an image representation resulting from the anatomy-fluoroscopy-registration.

* * * * *